(12) United States Patent
Goldfarb et al.

(10) Patent No.: US 11,806,493 B2
(45) Date of Patent: Nov. 7, 2023

(54) SYSTEMS, APPARATUS, AND METHODS FOR TRANSPORT AND DELIVERY OF THERAPEUTIC SUBSTANCE TO MIDDLE EAR

(71) Applicant: TUSKER MEDICAL, INC., Menlo Park, CA (US)

(72) Inventors: Eric Goldfarb, Belmont, CA (US); Mahyar Z. Kermani, San Ramon, CA (US); Rohit Girotra, San Francisco, CA (US)

(73) Assignee: Tusker Medical, Inc., Menlo Park, CA (US)

( * ) Notice: Subject to any disclaimer, the term of this patent is extended or adjusted under 35 U.S.C. 154(b) by 690 days.

(21) Appl. No.: 16/964,773

(22) PCT Filed: Feb. 1, 2019

(86) PCT No.: PCT/US2019/016389
§ 371 (c)(1),
(2) Date: Jul. 24, 2020

(87) PCT Pub. No.: WO2019/152866
PCT Pub. Date: Aug. 8, 2019

(65) Prior Publication Data
US 2021/0052868 A1 Feb. 25, 2021

Related U.S. Application Data

(60) Provisional application No. 62/625,933, filed on Feb. 2, 2018.

(51) Int. Cl.
*A61F 11/20* (2022.01)
*A61M 31/00* (2006.01)

(52) U.S. Cl.
CPC ...... *A61M 31/00* (2013.01); *A61M 2205/0233* (2013.01); *A61M 2205/35* (2013.01); *A61M 2210/0668* (2013.01)

(58) Field of Classification Search
CPC ......... A61F 11/202; A61M 2210/0668; A61M 31/002
See application file for complete search history.

(56) References Cited

U.S. PATENT DOCUMENTS 5,769,884 A * 6/1998 Solovay .................... A61F 2/07
623/1.13
8,052,693 B2 11/2011 Shahoian
(Continued)

OTHER PUBLICATIONS

Chinese Application No. 201980007098.4 Text Of First Office Action & Search Report dated Jun. 21, 2022.
(Continued)

*Primary Examiner* — Deanna K Hall
(74) *Attorney, Agent, or Firm* — Dickinson Wright PLLC

(57) ABSTRACT

Systems, apparatus, and methods are described for transporting and delivering a therapeutic substance to an ear of a subject, including a tubular element (216) configured for deployment in a tympanic membrane (TM) and a fluid transport element (230). The fluid transport element can be configured to transport the therapeutic substance from a proximal side to a distal side of the tubular element. Systems, apparatus, and methods further can include a fluid dispenser including a reservoir configured to contain a therapeutic substance, and a tubular element defining a lumen in fluid communication with an outlet in which the lumen and the outlet are configured to deliver the therapeutic substance from the reservoir to a region proximal to the tympanic membrane. Systems, apparatus, and methods further can include an electrode device.

20 Claims, 16 Drawing Sheets

(56) References Cited

U.S. PATENT DOCUMENTS

| | | | |
|---|---|---|---|
| 8,864,774 | B2 | 10/2014 | Liu et al. |
| 9,011,363 | B2 | 4/2015 | Clopp et al. |
| 9,320,652 | B2 | 4/2016 | Andreas et al. |
| 9,326,943 | B1 * | 5/2016 | Skovlund ............. A61K 9/1658 |
| 9,681,891 | B2 | 6/2017 | Andreas et al. |
| 9,833,360 | B2 | 12/2017 | Andreas et al. |
| 2008/0262468 | A1 * | 10/2008 | Clifford ................ A61M 31/00 604/501 |
| 2016/0038342 | A1 | 2/2016 | Van et al. |
| 2019/0321610 | A1 | 10/2019 | Goldfarb et al. |

OTHER PUBLICATIONS

International Search Report and Written Opinion from European Patent Office (EPO/ISA) dated May 15, 2019 for PCT application No. PCT/US2019/016389 filed Feb. 1, 2019; 12 pages.

McCall, Andrew A, et al.; "Drug Delivery for Treatment of Inner Ear Disease: Current State of Knowledge," Ear and Hearing: Official Journal of the American Auditory Society, vol. 31—Issue 2, Apr. 2010, pp. 156-165, USA.

Chinese Application No. 201980007098.4 Text of Second Office Action & Search Report dated Dec. 26, 2022.

* cited by examiner

SYSTEMS, APPARATUS, AND METHODS FOR TRANSPORT AND DELIVERY OF THERAPEUTIC SUBSTANCE TO MIDDLE EAR

CROSS-REFERENCE TO RELATED APPLICATIONS

This application is a U.S. National Phase Entry of PCT application Ser. No. PCT/US2019/016389 filed Feb. 1, 2019 and titled "SYSTEMS, APPARATUS, AND METHODS FOR TRANSPORT AND DELIVERY OF THERAPEUTIC SUBSTANCE TO MIDDLE EAR." The PCT application claims priority to U.S. Provisional Patent App. No. 62/625,933, filed Feb. 2, 2018, titled "SYSTEMS, APPARATUS, AND METHODS FOR TRANSPORT AND DELIVERY OF THERAPEUTIC SUBSTANCE TO MIDDLE EAR." The PCT application and the provisional application are both incorporated by reference herein.

TECHNICAL FIELD

The present disclosure relates generally to systems, apparatus, and methods for transporting and delivering a substance to an ear of a subject. More specifically, the present disclosure relates to systems, apparatus, and methods for transporting and delivering a therapeutic substance across a subject's tympanic membrane and into the middle ear or tympanic cavity.

BACKGROUND

In humans and many other animals, the tympanic cavity is a small cavity in the petrous temporal bone. As shown in FIG. 1, the tympanic cavity surrounds the bones of the middle ear, including the malleus, incus, and stapes, and is bounded by six walls. The convex lateral wall, which separates the tympanic cavity from the external auditory canal and outer ear, includes the tympanic membrane. The convex medial wall, which separates the tympanic cavity from the inner ear, includes the oval window, round window, and the promontory formed by the first turn of the cochlea. The roof separates the tympanic cavity from the cranial cavity, the floor separates the tympanic cavity from the jugular vein, the posterior wall separates the tympanic cavity from the mastoid antrum air cells, and the anterior wall separates the tympanic cavity from the carotid canal.

The tympanic cavity is hollow and normally filled with air; however, the air of the tympanic cavity usually is not in direct contact with the atmosphere of the outside environment. When a pressure difference develops between the tympanic cavity and the outside environment (e.g., because the subject moves between altitudes as on an airplane or dives into water), the tympanic membrane may become damaged if it is not relieved. If tympanic cavity pressure remains lower than the atmosphere, the tympanic membrane may retract into the tympanic cavity. If tympanic cavity pressure remains higher than the atmosphere, the tympanic membrane may rupture.

Otitis media is an inflammation of the middle ear (without reference to etiology or pathogenesis) and is particularly common in human children due to their anatomy and immune function. If severe or untreated, otitis media may result in rupture of the tympanic membrane, hearing loss, or intracranial complications. Otitis media may be managed using oral and topical pain killers (e.g., ibuprofen, acetaminophen, opiates, antipyrine, benzocaine ear drops) and antibiotics (e.g., amoxicillin, amoxicillin-clavulanate, beta lactamase inhibitor).

The Eustachian tube helps equalize middle ear pressure and drain fluid from the middle ear by connecting the tympanic cavity to the nasopharynx; however, Eustachian tubes are susceptible to inflammation and dysfunction.

To relieve pressure or pain from pressure differences and/or inflammation, the tympanic membrane may be punctured (e.g., by performing a myringotomy, tympanostomy, or tympanocentesis). Fluid present in the middle ear may be aspirated during a procedure. In some procedures, a tube or grommet is inserted into the tympanic membrane to drain fluid from the tympanic cavity.

After treatment of otitis media using surgery (e.g., by performing a myringotomy, tympanostomy, or tympanocentesis), it is common for a physician to prescribe antibiotics. For example, a physician may prescribe an antibiotic or other therapeutic substance in the form of ear drops to be administered by a patient at home for a period of time. Penetration of the therapeutic substance into the middle ear can depend on the viscosity of the therapeutic substance (or the fluid carrying the therapeutic substance), the wetting capability and geometry of an ear tube, and the technique used to administer the therapeutic substance. Oftentimes, because the therapeutic substance is administered by a patient or a parent and not by a physician, there is variability in technique, which can affect the efficacy of the prescribed treatment. Therefore, it is desirable to have methods and systems for transporting and delivering a therapeutic substance to the middle ear such that the process is less dependent on administration technique.

SUMMARY

Systems, apparatus, and methods are described for transporting and delivering a therapeutic substance to an ear of a subject. In some embodiments, a tubular element is deployable in a tympanic membrane, where the tubular element includes a body defining a lumen, a first flange disposed on a proximal end of the body, and a second flange disposed on a distal end of the body. A fluid transport element can be embedded in the body and configured to transport a therapeutic substance from the proximal end to the distal end of the body. In an embodiment, the fluid transport element includes a wicking material. In another embodiment, the fluid transport element includes microfluidic channels.

In some embodiments, a system for transporting and delivering a therapeutic substance includes a tympanostomy tube and a fluid dispenser. The fluid dispenser can include a reservoir configured to contain the therapeutic substance, and a tubular element defining a lumen in fluid communication with an outlet, where the lumen and the outlet are configured to deliver the therapeutic substance from the reservoir to a region of an ear canal proximal to the tympanic membrane, such that the therapeutic substance can be delivered to a middle ear distal to the tympanic membrane via the tympanostomy tube. In an embodiment, the system further includes a vibrating element configured to vibrate the ear canal to transport the therapeutic substance toward the tympanic membrane.

In some embodiments, a system for transporting and delivering a therapeutic substance includes a tympanostomy tube and an electrode device. The tympanostomy tube can include a first conductive element disposed at a proximal side and configured to form a first electrical path, and a second conductive element disposed at a distal side and configured to form a second electrical path. The tympanostomy tube can be configured to transport and deliver the therapeutic substance upon activation of the electrode device to modify the wetting properties of a surface of the tympanostomy tube.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 4A provides a side view of the fluid transport device, FIG. 4B provides a view of a proximal end of the fluid transport device, and FIG. 4C provides a view of the distal end of the fluid transport device.

FIG. 6A depicts the fluid transport device deployed in a tympanic membrane, and FIG. 6B provides an enlarged view of the fluid transport device.

FIG. 7A depicts the fluid transport device deployed in a tympanic membrane, and FIG. 7B provides an enlarged view of the fluid transport device.

DETAILED DESCRIPTION

Systems, apparatus, and methods are described herein for transporting and delivering a therapeutic substance to the middle ear or tympanic cavity.

Figure 1:
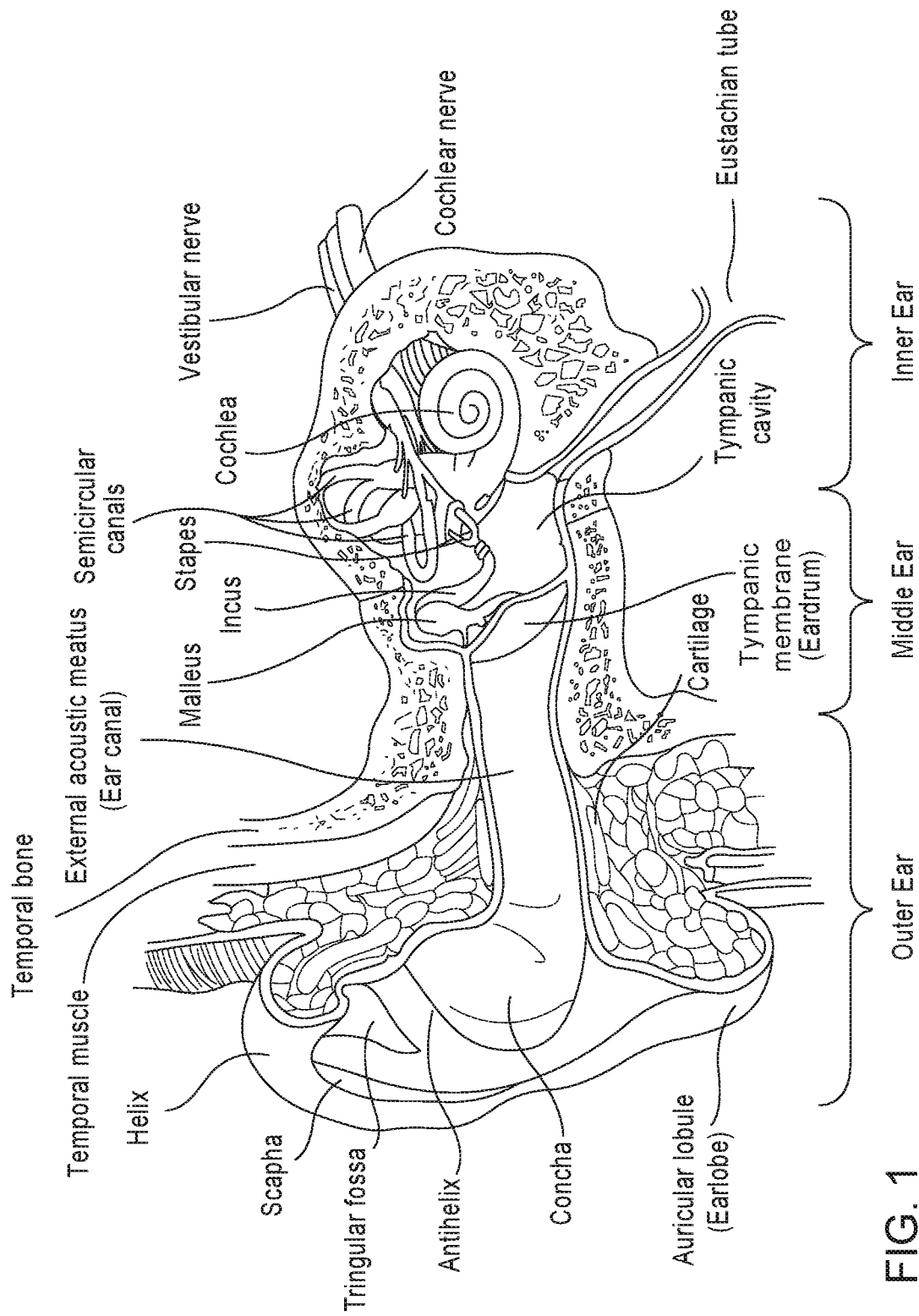
FIG. 1 illustrates the anatomy of the human ear.
Figure 2:
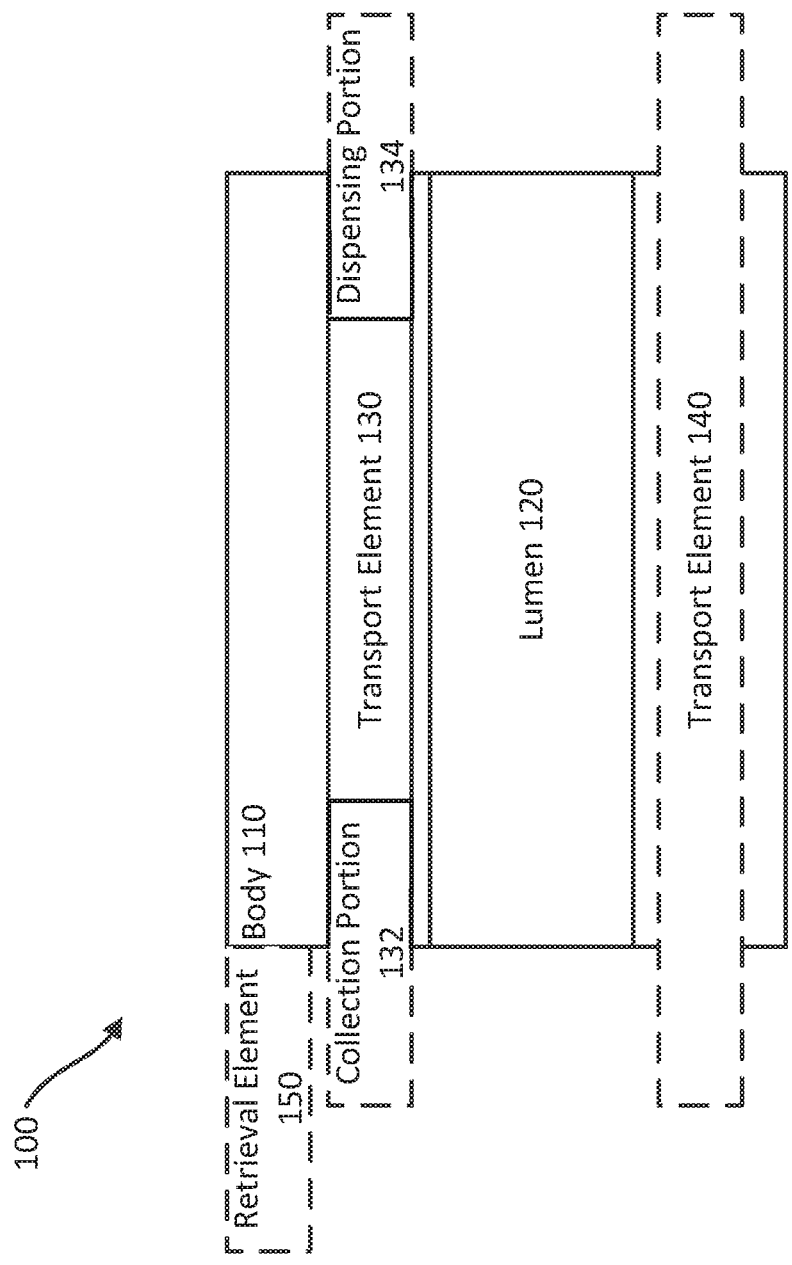
FIG. 2 is a schematic illustration of a fluid transport device, according to some embodiments.

As schematically illustrated in FIG. 2, a fluid transport system 100 can include a body 110 that defines a lumen 120. In an embodiment, fluid transport device 100 can be implemented as a tympanostomy tube with a body 110 including a tubular portion, a lateral flange, and a medial flange. Further detail regarding such an embodiment is provided with reference to FIG. 3, described below. Fluid transport device 100 can be deployed or position in an incision formed in a tympanic membrane. Lumen 120 can be designed to equalize pressure between the outer ear and the inner ear, for example, in a case of otitis media. Lumen 120 can be configured to transport a fluid (e.g., a gas or liquid) from one end of fluid transport device 100 to another end of fluid transport device 100. For example, when fluid transport device 100 is deployed in a tympanic membrane for treating otitis media, lumen 120 can be configured to transport a fluid (e.g., effusion within the tympanic cavity) from within the tympanic cavity to a proximal or lateral end of fluid transport device 100, thereby removing the fluid from within the tympanic cavity. In some embodiments, lumen 120 of fluid transport device 100 can be configured to transport a fluid from the ear canal to a distal or medial end of fluid transport device 100, thereby delivering a fluid from outside of the tympanic cavity into the tympanic cavity.

In some embodiments, lumen 120 can be configured and/or a component can be disposed within lumen 120 that can facilitate fluid transport through lumen 120. For example, structure such as artificial cilia, a wick, a vent channel, etc. can be disposed within lumen 120 to facilitate fluid transport through lumen 120. Alternatively or additionally, fluid transport can be shaped, e.g., have tapering regions and/or regions with grooves or other texture that can facilitate fluid transport.

Fluid transport device 100 can include a transport element 130. Optionally, in some embodiments, fluid transport device 100 can include one or more additional transport elements, e.g., transport element 140. Transport element 130 can be configured to transport a fluid, e.g., a therapeutic substance, from one end to another end of body 110. Transport element 130 can include a collection portion 132 and a dispensing portion 134. Collection portion 132 can be configured to collect fluid, and dispensing portion 134 can be configured to dispense fluid. In an embodiment, when fluid transport device 100 is deployed in a tympanic membrane, collection portion 132 can be disposed in the ear canal on a lateral side of the tympanic membrane and dispensing portion 134 can be disposed in the tympanic cavity on a medial side of the tympanic membrane. When positioned as such, collection portion 132 can be configured to collect fluid from the lateral side, which can be transported via transport element 130 to the medial side, and dispensing portion 134 can be configured to release the fluid into the tympanic cavity or middle ear.

Transport element 130 can extend from one end to the other end of body 110. In some embodiments, transport element 130 can optionally extend beyond one or both ends of body 110. For example, a portion of collection portion 132 can extend beyond a proximal end of body 110, such that, when fluid transport device 100 is deployed in the tympanic membrane, that portion of collection portion 132 can extend into the ear canal. Collection portion 132, by extending into ear canal, can increase an area from which collection portion 132 can collect a fluid, thereby promoting fluid collection. In some embodiments, collection portion 132 can extend a sufficient distance into ear canal toward an opening of the ear such that a physician can engage collection portion 132 (e.g., a physician can grasp or grip collection portion 132, either directly or via an instrument) to retrieve fluid transport device 100. Alternatively or additionally, a portion of dispensing portion 134 can extend beyond a distal end of body 110, such that, when fluid transport device 100 is deployed in the tympanic membrane, that portion of dispensing portion 134 can extend into the tympanic cavity or middle ear. In some embodiments, having one or both ends of transport element 130 extend into the ear canal and/or tympanic cavity can promote collection and/or delivery of fluids from and to specific regions of the ear of a subject. For example, having a proximal end of transport element 130 extend into the ear canal can promote collection of fluids from a region of the ear canal that is not immediately adjacent to the tympanic membrane and/or fluid transport device 100. And, for example, having a distal end of transport element 130 extend into the tympanic cavity can enable delivery of a fluid deeper into tympanic cavity, e.g., to the round window or some other part of the middle ear and/or inner ear anatomy.

Fluid transport device 100 optionally can include a retrieval element 150 for retrieving fluid transport device 100. In some embodiments, such as those described above where a proximal end of transport element 130 extends sufficiently into ear canal such that it can be engaged by a physician, retrieval element 150 and transport element 150 can be one and the same. In other embodiments, retrieval element 150 can be separate from transport element 130, e.g., a separate structure that can be attached to body 110 and extend from body 110 into ear canal toward an opening of the ear canal. An individual such as, for example, a physician, can grip the retrieval element 150, either directly or via an instrument, to remove fluid transport device 100 from the ear.

The transport rate and/or delivery rate of the fluid through transport element 130 can be controlled by the geometry, configuration, and/or material of transport element 130. For example, a transport element 130 with a larger diameter can enable faster flow rates than a transport element 130 with a small orifice or small diameter region. As another example, a transport element 130 including multiple channels may enable a faster flow rate than a transport element 130 with fewer channels.

Figure 3:
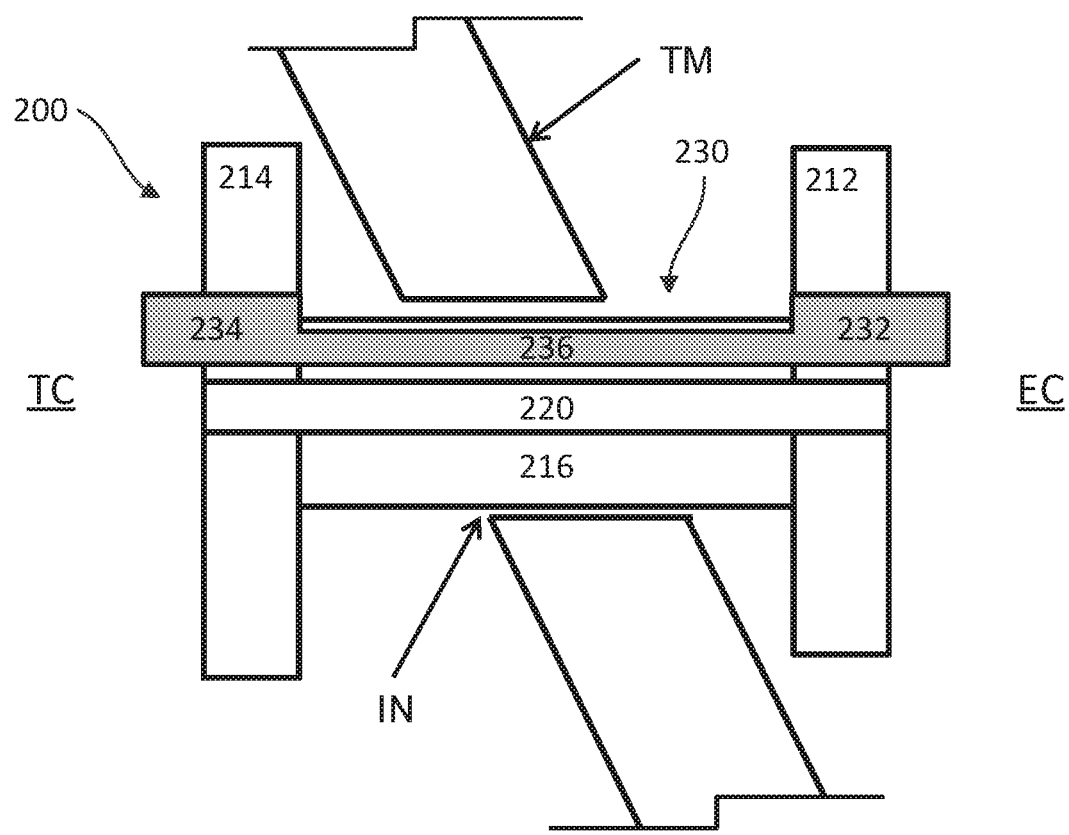
FIG. 3 is a schematic illustration of a fluid transport device deployed in a tympanic membrane, according to some embodiments.

FIG. 3 schematically illustrates a fluid transport device implemented as a tympanostomy tube 200. Tympanostomy tube 200 includes a body having a lateral flange 212 disposed on a proximal end of tympanostomy tube 200, a medial flange 214 disposed on a distal end of tympanostomy tube 200, and a tubular portion 216 extending from lateral flange 212 to medial flange 214. Tubular portion 216 can define a lumen 220. In some embodiments, tympanostomy tube can include components that are structurally and/or functionally similar to those of tympanostomy tubes disclosed in U.S. Pat. No. 9,011,363, titled "Tympanic membrane pressure equalization tube," issued Apr. 21, 2015, and U.S. Provisional Application No. 62/371,583, titled "Systems, Apparatus, and Methods for Delivery of Therapeutic Substance to the Middle and/or Inner Ear." The disclosures of each of these references are incorporated herein by reference.

Tympanostomy tube 200 can be deployed in an incision IN formed in a tympanic membrane TM such that lateral flange 212 is disposed within ear canal EC and medial flange 214 is disposed within tympanic cavity TC. In some embodiments, incision IN can be formed in tympanic membrane TM and/or tympanostomy tube 200 deployed in tympanic membrane TM using a tympanostomy tube delivery system. Examples of tympanostomy tube delivery systems are disclosed in U.S. Pat. No. 8,052,693, titled "System and Method for the Simultaneous Automated Bilateral Delivery of Pressure Equalization Tubes," issued Nov. 8, 2011; U.S. Pat. No. 8,864,774, titled "Tympanic Membrane Pressure Equalization Tube Delivery System," issued Oct. 21, 2014; U.S. Pat. No. 9,320,652, titled "Features to Improve and Sense Tympanic Membrane Apposition by Tympanostomy Tube Delivery Instrument," issued Apr. 26, 2016; U.S. Pat. No. 9,681,891, titled "Tympanostomy Tube Delivery Device with Cutting Dilator," issued Jun. 20, 2017; U.S. Patent Application Publication No. 2016/0038342, titled "Tympanostomy Tube Delivery Device with Rotatable Flexible Shaft," published Feb. 11, 2016; and U.S. Pat. No. 9,833,360, titled "Tympanostomy Tube Delivery Device with Replaceable Shaft Portion," issued Dec. 5, 2017. The disclosures of each of these references are incorporated herein by reference. For example, a tympanostomy tube delivery system including a cutter, a dilator, a shield, and a pusher can be used to form incision IN, dilate incision IN, and/or deploy tympanostomy tube 200 in incision IN. In some embodiments, incision IN can be formed using a myringotomy device, and then tympanostomy tube 200 can be placed within incision IN.

Tympanostomy tube 200 can be formed of a shape memory material, and can be compressed for delivery within a tympanostomy tube delivery system. For example, lateral flange 212 and medial flange 214 of tympanostomy tube 200 can be compressed such that they extend longitudinally from tubular body 216 and placed within a tubular shaft of a tympanostomy tube delivery system. After being deployed, tympanostomy tube 200 can expand to its original or uncompressed state such that lateral flange 212 and medial flange 214, disposed on opposite sides of tympanic membrane TM, can retain tympanostomy tube 200 within tympanic membrane TM.

Tympanostomy tube 200 also includes a transport element 230 with a collection portion 232, a transport portion 236, and a dispensing portion 234. Collection portion 232 and dispensing portion 234 can be functionally similar to collection portion 132 and dispensing portion 134. That is, collection portion 232 can be configured to collect a fluid, e.g., a therapeutic substance, and dispensing portion 134 can be configured to dispense the fluid. When tympanostomy tube 200 is deployed in tympanic membrane TM, collection portion 232 can intake and/or collect fluid from ear canal EC, and dispensing portion 234 can dispense the fluid into tympanic cavity TC. Collection portion 232 can be configured to extend and/or fan out to cover a large area such that it can collect more fluid, whereas dispensing portion 234 can be configured to promote droplet formation of the fluid such that drops of the fluid can be released in tympanic cavity TC. Transport portion 236 can extend between collection portion 232 and dispensing portion 234 and function to encourage passage of the fluid through tympanostomy tube 200. Each of collection portion 232, dispensing portion 234, and transport portion 236 can have different geometries and/or configurations, or include and/or be formed of different material, as appropriate to serve its function.

Transport element 230 can be coupled to, integrated into, and/or embedded within the body of tympanostomy tube 200. In some embodiments, the body of tympanostomy tube 200 and transport element 230 can be formed together as a unitary component, e.g., via injection molding or other processes. In other embodiments, the body of tympanostomy tube 200 and transport element 230 can be formed separately and then joined together (e.g., via an attachment means such as an adhesive, a fastener, etc.), or one of the body of tympanostomy tube 200 or transport element 230 can be formed first and the other can be formed around the first formed component (e.g., transport element 230 can be formed, and then the body of tympanostomy tube 200 can be formed around transport element 230, such as via injection molding).

Figure 4A:
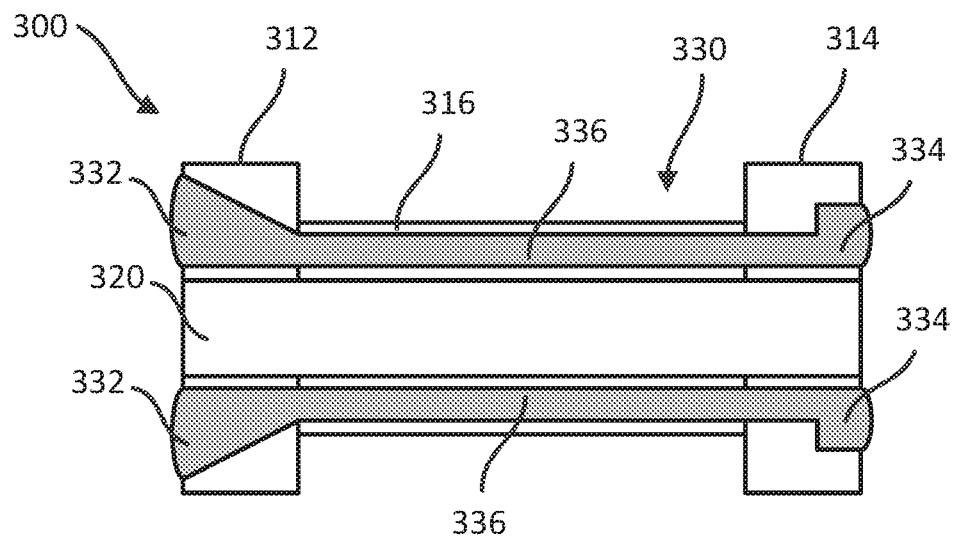
FIGS. 4A-4C are schematic illustrations a fluid transport device, according to some embodiments.
Figure 4B:
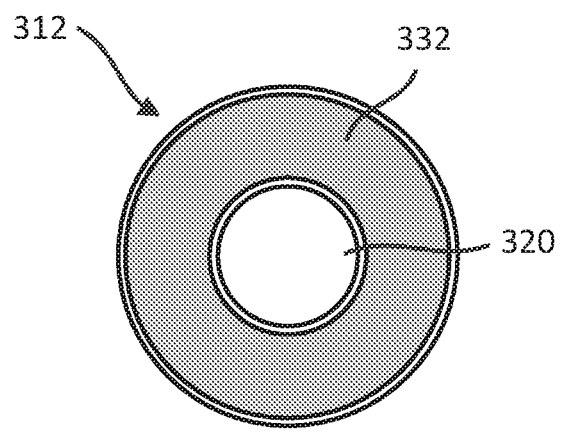
Figure 4C:
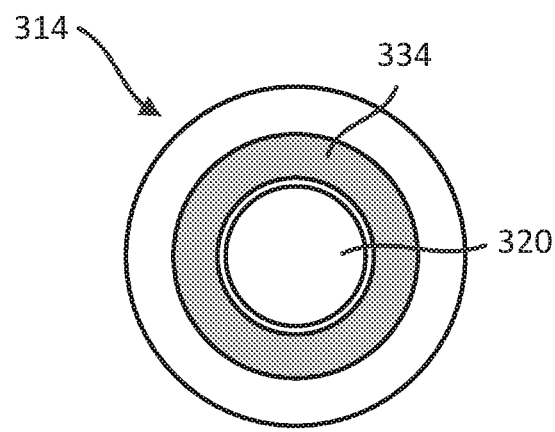

FIGS. 4A, 4B, and 4C schematically illustrate an example fluid transport device implemented as a tympanostomy tube 300. Similar to tympanostomy tube 200, tympanostomy tube 300 includes a body with a lateral flange 312, a medial flange 314, and a tubular portion 316 that defines a lumen 320. Tympanostomy tube 300 also includes a transport element 330, which can be coupled to and/or embedded within the body of tympanostomy tube 300. Transport element 330 includes a first portion 332 (e.g., a collection portion) that is coupled to and/or embedded within lateral flange 312, a second portion 334 (e.g., a dispensing portion) that is coupled to and/or embedded within medial flange 314, and a third portion 336 (e.g., a transport portion) that extends between portions 332 and 334 and is coupled to and/or embedded within tubular portion 316.

In some embodiments, transport element 330 is formed of a wicking material. As depicted in FIG. 4B, which provides a view of a proximal end of tympanostomy tube 300, first portion 332 of transport element 330 can cover a substantial area of lateral flange 312, e.g., the wicking material can be fanned out on the lateral side, such that transport element 330 can promote greater fluid collection (e.g., by having a greater surface area that comes into contact with fluid in the outer ear). As depicted in FIG. 4C, which provides a view of a distal end of tympanostomy tube 300, Second portion 334 of transport element 330 can be more focally configured on medial flange 314, e.g., the wicking material can be more focused or bundled on the medial side, such that it can promote formation of drops of fluid for release into the middle ear. Transport element 330 can extend from the lateral side to the medial side of tympanostomy tube 300 such that it can transport a fluid (e.g., a therapeutic substance) from the external ear (e.g., ear canal) to the middle ear.

Figure 5:
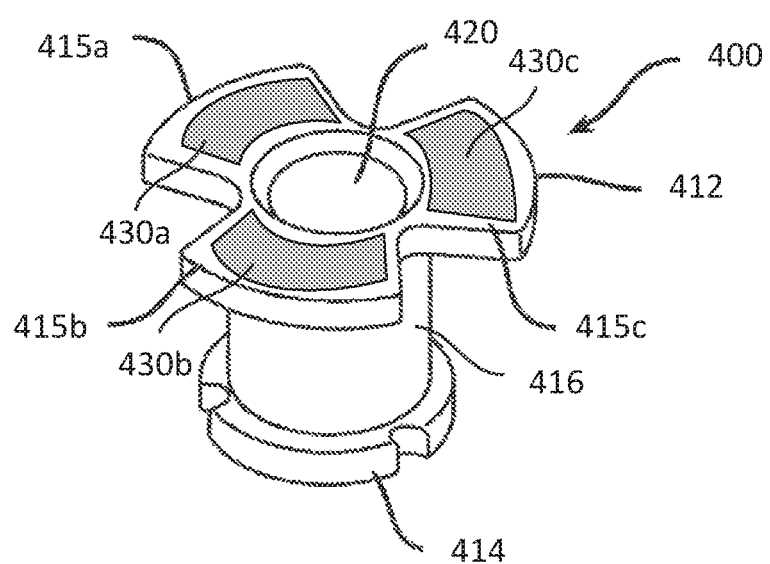
FIG. 5 provides a perspective view of a fluid transport device, according to some embodiments.

While lateral flange 312 and medial flange 314 are depicted as having similar dimensions and configurations in FIGS. 4A-4C, one of ordinary skill in the art would understand that lateral flange 312 and medial flange 314 can have different dimensions and/or configurations. For example, as depicted in FIG. 5, a tympanostomy tube 400 can include asymmetric flanges. Tympanostomy tube 400 can include a lateral flange 412 and a medial flange 414. Lateral flange 412 can have an outer diameter that is greater than that of medial flange 414. Lateral flange 412 can have three retention elements 415a, 415b, and 415c. Retention elements 415a, 415b, and 415c can be of equal size and shape, as depicted in FIG. 5, or alternatively, in other embodiments, retention elements 415a, 415b, and 415c can be sized and shaped differently from one another. Retention elements 415a, 415b, and 415c can be evenly spaced around a circumference of a lumen 420 of a tubular body 416, i.e., retention elements 415a, 415b, and 415c are spaced 120 degrees apart.

Medial flange 414 can have one or more retention elements that are spaced around a circumference of tubular body lumen 420. The spaces separating the retention elements of lateral flange 412 can align with the spaces separating the retention elements of medial flange 414, as depicted in FIG. 5, or alternatively, in other embodiments, the spaces between the retention elements of the two flanges 412, 414 can be offset from one another.

Tympanostomy tube 400 can include one or more transport elements 430a, 430b, and 430c. Transport elements 430a, 430b, and 430c can be structurally and/or functionally similar to other transport elements disclosed herein (e.g., transport element 330). For example, transport elements 430a, 430b, and 430c can extend from one end to the other end of tympanostomy tube 400, e.g., from lateral flange 412 to medial flange 414. Transport elements 430a, 430b, and 430c can be connected to one another at a point along a length of tubular body 416 of tympanostomy tube 400, or remain separate from one another along the length of tubular body 416. Transport elements 430a, 430b, and 430c can be similarly shaped and dimensioned or, alternatively, have different shapes and/or dimensions. In an embodiment, transport elements 430a, 430b, and 430c can each be embodied as a wick (or formed of a wicking material) that is embedded into and extends along a length of tubular body 416.

When tympanostomy tube 400 is deployed in a tympanic membrane, lateral flange 412 can be disposed in the external ear, e.g., in the ear canal, and medial flange 414 can be disposed in the middle ear, e.g., the tympanic cavity. Transport elements 430a, 430b, and 430c can extend from the lateral side to the medial side of tympanostomy tube 400 such that it can transport a fluid (e.g., a therapeutic substance) from the external ear to the middle ear when tympanostomy tube 400 is so deployed. Similar to transport element 330, transport elements 430a, 430b, and 430c can cover a larger surface area on the lateral side of tympanostomy tube 400 (e.g., can cover a substantial portion of lateral flange 412 or be fanned out) than on the medial side of tympanostomy tube 400, such that transport elements 430a, 430b, and 430c can promote collection of fluid on the lateral side and promote formation of drops of fluid and/or release of fluid on the medial side.

Figure 6A:
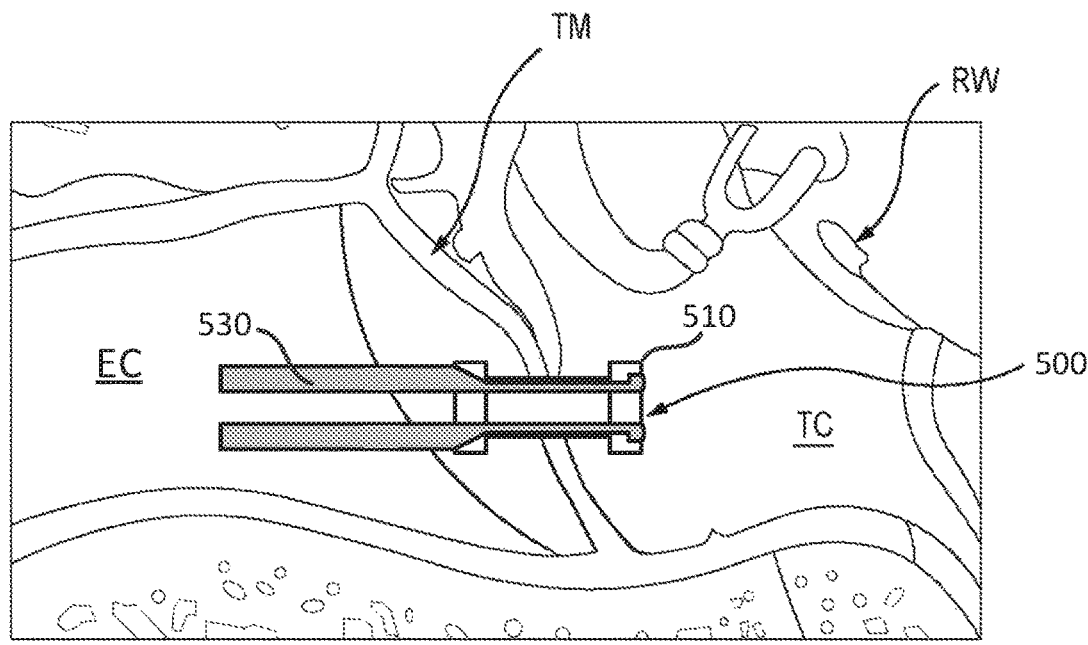
FIGS. 6A and 6B are schematic illustrations of a fluid transport device, according to some embodiments.
Figure 6B:
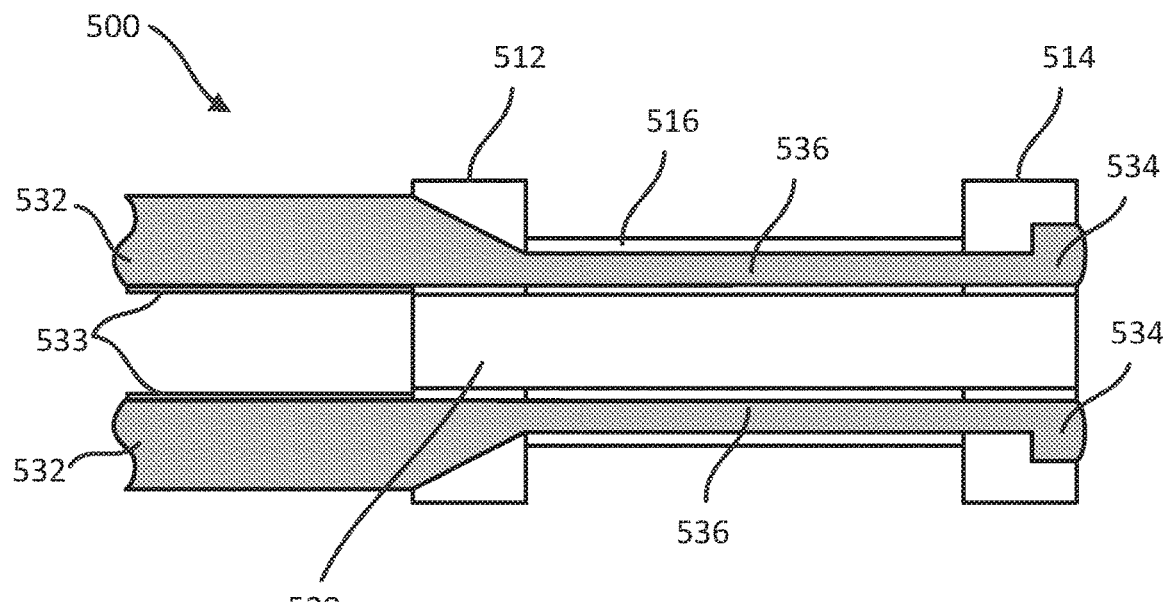

FIGS. 6A and 6B schematically illustrate an example fluid transport device implemented as a tympanostomy tube 500. Tympanostomy tube 500 includes components that can be structurally and/or functionally similar to those of other tympanostomy tubes described herein (e.g., tympanostomy tubes 300 and 400). For example, tympanostomy tube 500 can include a lateral flange 512, a medial flange 514, and a tubular portion 516 that defines a lumen 520. Tympanostomy tube 500 also includes a transport element 530, which can be coupled to and/or embedded within the body of tympanostomy tube 500. In some embodiments, transport element 530 can be formed of a wicking material. Transport element 530 can include three portions 532, 534, and 536 that are shaped and dimensioned differently from one another. First portion 532 (e.g., a collection portion) can be disposed on a proximal end of tympanostomy tube 500 and can extend a distance beyond lateral flange 512 into ear canal EC, as depicted in FIG. 6A. First portion 532, by extending beyond lateral flange 512 and into ear canal EC, can be configured to collect a greater amount of fluid from ear canal EC (e.g., via its greater exposed surface area and potential contact with more fluid in the ear canal EC). In some embodiments, first portion 532 can also facilitate removal of tympanostomy tube 500 from ear canal. For example, first portion 532 can act as an extension of tympanostomy tube 500 that can be engaged by a user (e.g., a physician) using an instrument for retrieval of tympanostomy tube 500 from the ear, e.g., in a case where the tube deployment was unsuccessful. Second portion 534 (e.g., a dispensing portion) can be disposed on a distal end of tympanostomy tube 500, and third portion 536 (e.g., a transport portion) can extend between first portion 532 and second portion 534 of transport element 530.

When tympanostomy tube 500 is deployed in tympanic membrane TM, lateral flange 512 can be disposed in the external ear, e.g., in ear canal EC, and medial flange 514 can be disposed in the middle ear, e.g., tympanic cavity TC. Transport element 530 can transport a fluid (e.g., a therapeutic substance) from ear canal EC to tympanic cavity TC when tympanostomy tube 500 is so deployed. Similar to transport element 330, transport element 530 can fan out (e.g., expand outwards) on the lateral side of tympanostomy tube 500, such that transport element 530 can promote collection of fluid on the lateral side. A distal end of transport element 530 (e.g., third portion 534) can also be configured to enable formation of drops of fluid and/or release of fluid on the medial side in the tympanic cavity TC.

Figure 7A:
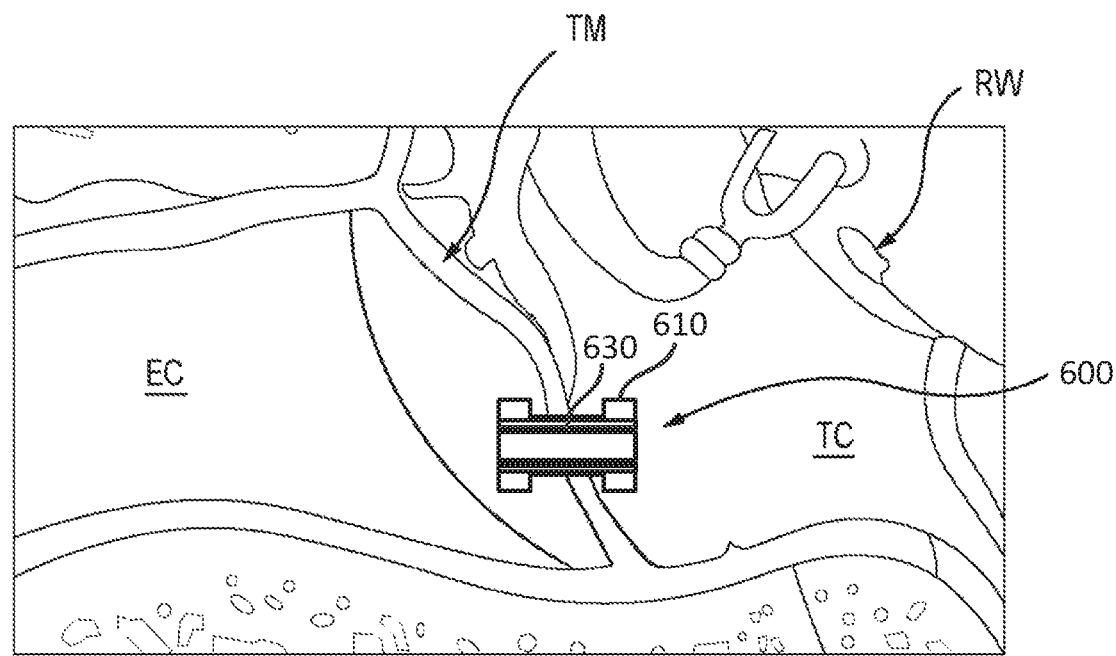
FIGS. 7A and 7B are schematic illustrations of a fluid transport device, according to some embodiments.
Figure 7B:
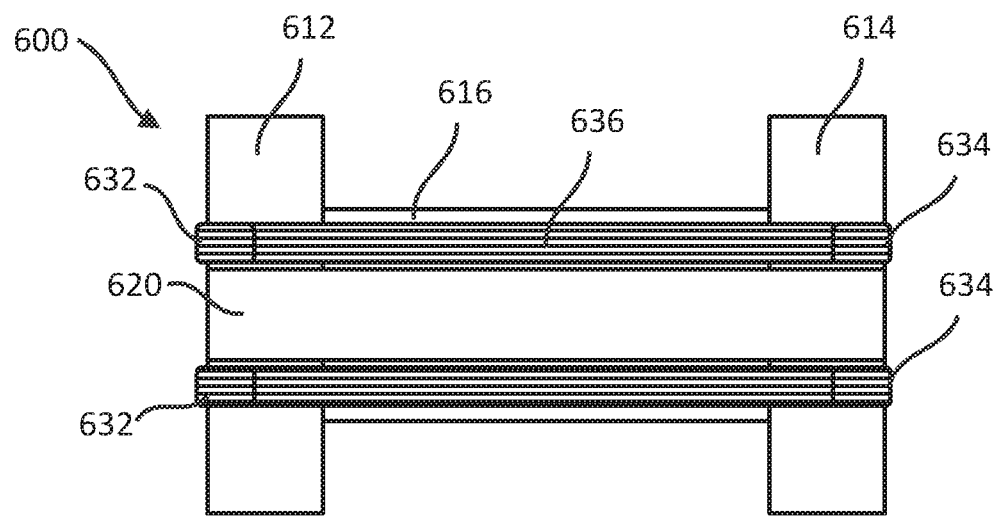

FIGS. 7A and 7B depict a fluid transport device implemented as a tympanostomy tube 600. Tympanostomy tube 600 can include includes components that can be structurally and/or functionally similar to those of other tympanostomy tubes described herein (e.g., tympanostomy tubes 300, 400, and 500). For example, tympanostomy tube 600 can include a lateral flange 612, a medial flange 614, and a tubular portion 616 that defines a lumen 620. Tympanostomy tube 600 also includes a transport element 630.

In an embodiment, transport element 630 can include one or more microfluidic channels. The microfluidic channels can be molded directly into body 610 of tympanostomy tube 600, or alternatively, the microfluidic channels can be coupled to (e.g., via a fastener and/or an adhesive) to tympanostomy tube. The microfluidic channels can be configured for fluid collection, fluid transport, fluid mixing, and/or fluid droplet formation. The microfluidic channels can be designed for a range of viscosities of fluid for delivery into the middle ear, e.g., ear drop fluids such as an antibiotic liquid or other liquid therapeutic substance for treatment of otitis media. The microfluidic channels can have different geometry (e.g., different shape and/or structure) at different points along tubular portion 616 to promote fluid collection, fluid transport, fluid mixing, and/or fluid droplet formation. For example, a first portion 632 of the microfluidic channels on a lateral side of tympanostomy tube 600 (e.g., along lateral flange 612) can be shaped and/or structured to collect fluid from ear canal EC, such as, for example, ear drop fluid administered into ear canal EC. The shape and/or structure of the microfluidic channels can then convert into different shape and/or structure in a second portion 636 to enable transport of fluid through tympanostomy tube 600. As the microfluidic channels reach a medial side of tympanostomy tube 600, the shape and/or structure of the microfluidic channels can convert again into a different shape and/or structure to enable droplet formation of the fluid and release of the fluid into tympanic cavity TC or the middle ear.

Figure 15B:
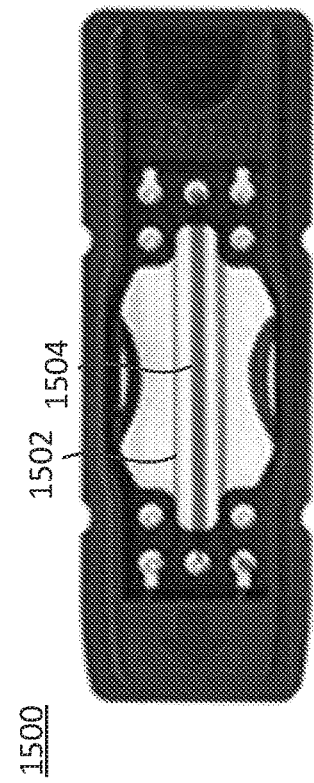
FIGS. 15A, 15B, 15C, and 15D depict different examples of microfluidic channels, according to some embodiments.
Figure 15A:
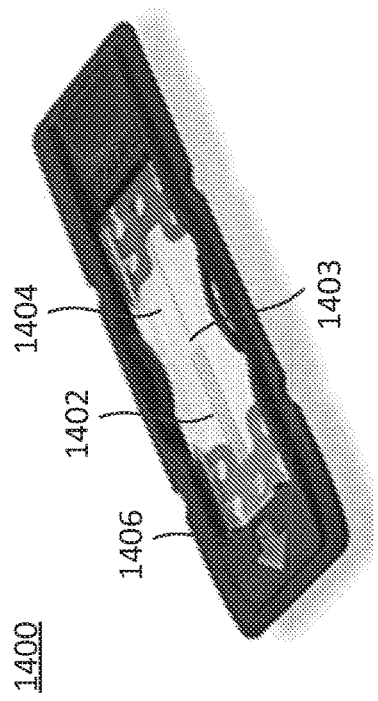
Figure 15D:
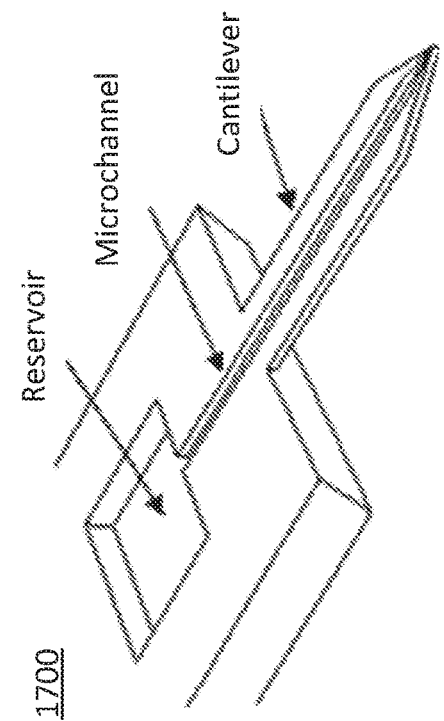
Figure 15C:
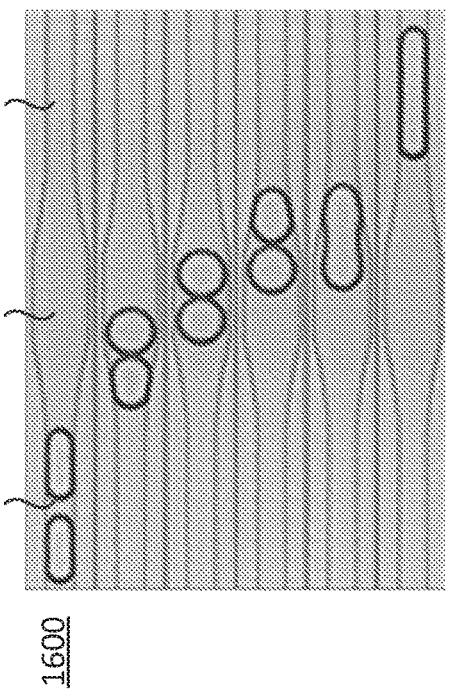

FIGS. 15A-15D provide examples of different configurations and/or geometries of microfluidic channels that are configured to enable different fluid flow characteristics. FIG. 15A depicts example microfluidic channels 1400 that are configured to generate droplets of fluid. Microfluidic channels 1400 can be provided on a microfluidic chip. Microfluidic channels 1400 include a first region 1404 having a single microfluidic channel that converts into a second region 1402 with a plurality of microfluidic channels. A nozzle 1403 can be configured to generate droplets of a fluid (e.g., a therapeutic substance) as the fluid pass from first region 1402 to second region 1404, as represented by an arrow 1406. FIG. 15B depicts microfluidic channels 1500 representing a flow cell that can transport a fluid (e.g., a therapeutic substance). Microfluidic channels 1500 can include channels having different outer diameters. For example, a first set of channels 1502 can have an outer diameter that is smaller than that of a second set of channels 1504. FIG. 15C depicts droplet transport through microfluidic channels having a first region 1602 with a first geometry, that transitions into a second region 1604 with a second geometry, that in turn transitions into a third region 1606 with a third geometry. An outer diameter of second region 1604 may be greater than that of first and third regions 1602, 1606. When droplets of a fluid travel along a length of microfluidic channels 1600, such droplets can encounter the larger diameter of second region 1604 and collide. Then when the droplets pass into the smaller diameter of third region 1606, the droplets may merge together. FIG. 15D depicts an example 1700 of a reservoir that leads to a microchannel.

Figure 8:
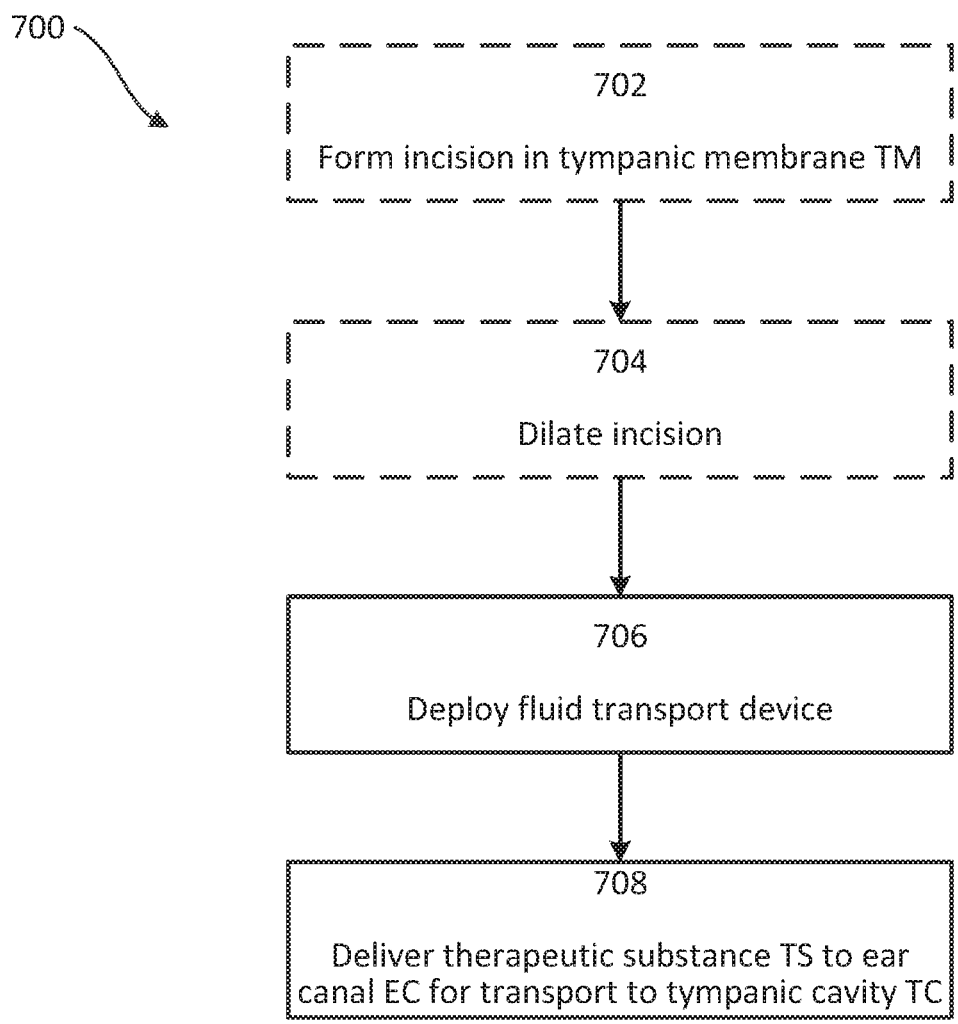
FIG. 8 is a flow diagram illustrating a method for transporting and delivering a therapeutic substance to a middle ear or tympanic cavity of a subject in accordance with some embodiments.

FIG. 8 is a flow diagram illustrating a method 700 of transporting and delivering a fluid, such as a therapeutic substance to a tympanic cavity TC or the middle ear. To reach tympanic cavity TC, an incision IN through tympanic membrane TM is required. Incision IN may already have been created in a separate procedure on the subject, e.g. by a myringotomy or tympanocentesis to enable drainage of medial effusion, or by a tympanostomy in connection with delivery of a tympanostomy tube. Alternatively, formation of incision IN may be performed as an initial step 702. Incision IN may be formed using any suitable technique and device.

Incision IN may also be dilated, either as part of a separate procedure, e.g., in connection with delivery of a tympanostomy tube, or as step 704 of method 700. The dilation can facilitate insertion of a fluid transport device, such as, for example, fluid transport device 100 or tympanostomy tubes 200, 300, 400, 500, and 600, as described above. Incision IN may be dilated using any suitable technique and device.

In step 706, a fluid transport device, such as, for example, fluid transport device 100 or tympanostomy tubes 200, 300, 400, 500, and 600, as described above, is deployed. Deployment of fluid transport device can involve disposing fluid transport device into incision IN with a first portion of fluid transport device (e.g., a lateral flange or proximal end of fluid transport device) disposed on one side of tympanic membrane TM and a second portion of fluid transport device (e.g., a medial flange or a distal end of fluid transport device) disposed on the other side of tympanic membrane TM.

Therapeutic substance TS then can be delivered to tympanic cavity TC, at step 708. Although FIG. 8 illustrates method 700 as occurring in a certain order, the ordering of method 700 can be modified. Additionally, certain of the steps can be performed concurrently in a parallel process when possible, as well as performed sequentially. For example, in some embodiments, step 708 (delivering therapeutic substance to tympanic cavity TC) can be performed simultaneously with step 706 (deployment of tympanostomy tube).

Figure 9:
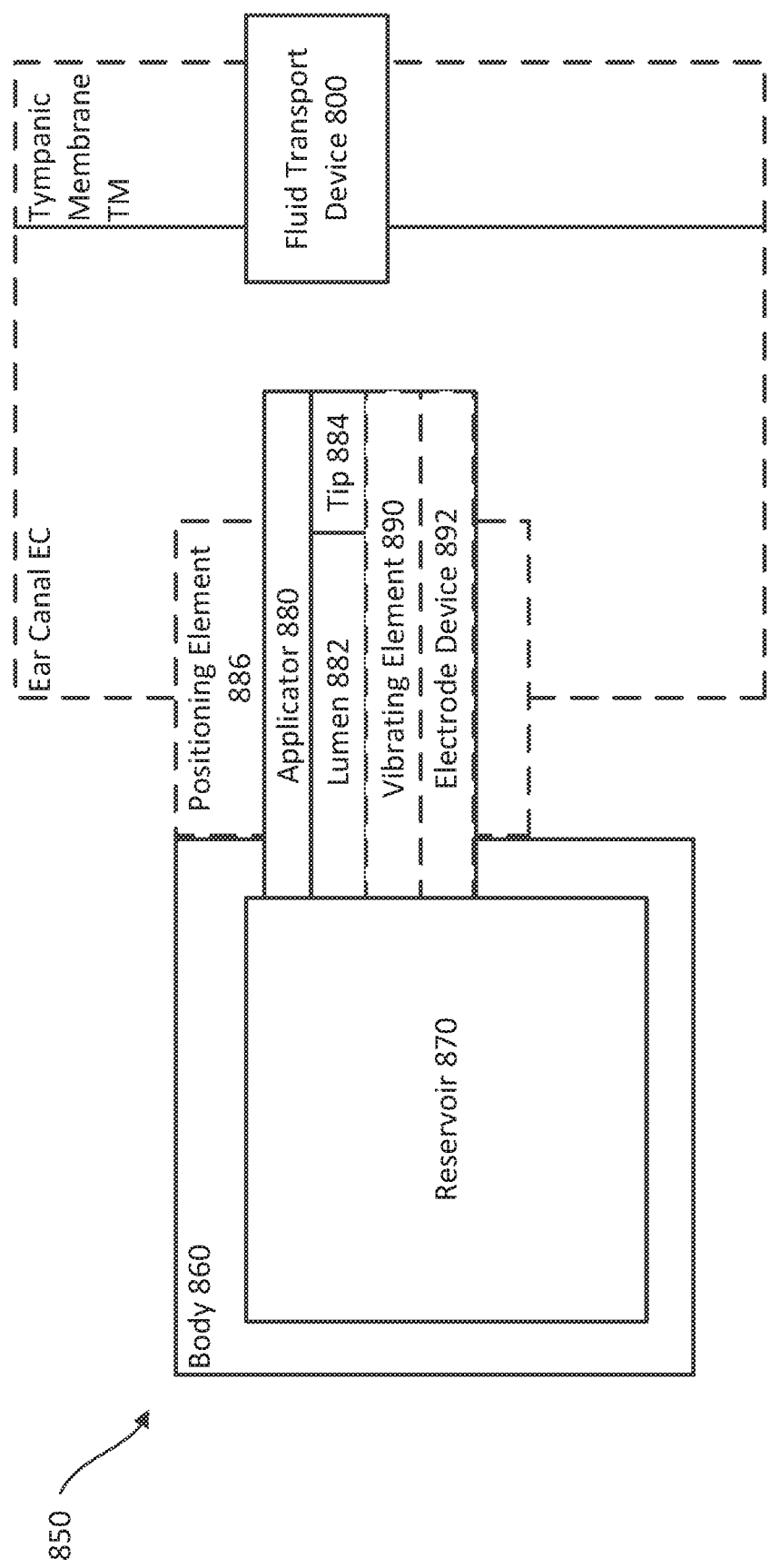
FIG. 9 is a schematic illustration of a fluid transport system including a fluid dispenser or accessory device to be used with a tympanostomy tube, according to some embodiments.

FIG. 9 schematically illustrates a fluid transport system, including an accessory device, such as, for example, a fluid dispenser 850, that can be used with a fluid transport device 800. Fluid delivery device 800 can be structurally and/or functionally similar to fluid transport device 100 or tympanostomy tubes 200, 300, 400, 500, and 600, described above. As depicted in FIG. 9, fluid transport device 800 can be deployed in a tympanic membrane TM.

Fluid dispenser 850 can include a body 860 and a reservoir 870. Reservoir 870 can contain a therapeutic substance. An applicator 880 defining a lumen 882 can be coupled fluidically to reservoir 870 such that the therapeutic substance within reservoir 870 can exit through lumen 882 and be delivered into ear canal EC. Fluid dispense 850 can include a tip 884 that includes a plurality of spay holes. Tip 884 can direct the therapeutic substance toward tympanic membrane TM.

Conventional applicators that place a therapeutic substance in the form of ear drops in a subject's ear canal may not enable those ear drops to reach the tympanic membrane and/or a deployed tympanostomy tube. To move the ear drops toward the tympanic membrane, the subject may need to angle his or her ear canal (e.g., orient his or her ear canal vertically) to enable gravity to pull the therapeutic substance toward the tympanic membrane. Alternatively or additionally, tragal pumping, or pushing on the subject's tragus, may be needed to move the therapeutic substance toward the tympanic membrane. Oftentimes, even when instructed to do so and on how to do so, the subject or another independent may forget to perform tragal pumping or perform it improperly, thereby reducing an amount of therapeutic substance that reaches the tympanic membrane and the efficacy of the therapeutic substance. Applicator 880 and tip 884 can deliver the therapeutic substance to a region of ear canal proximate to tympanic membrane TM and fluid transport device 800 (if deployed in tympanic membrane TM) without relying on gravity and/or user action, such as, for example, tragal pumping.

Optionally, fluid dispenser 850 can also include a vibrating element 890. Vibrating element 890 can be configured to vibrate ear canal EC. Vibrating element 890 can include a motor that can apply a vibrating motion to a component that can fit on applicator 880 and/or an area of the ear proximate to ear canal EC (e.g., the tragus or behind the ear proximate to the mastoid bone of the ear). Vibrating element 890 can be powered using a battery (not depicted) that can be carried on fluid dispenser 850. In alternative embodiments, vibrating element 890 can be provided separately from fluid dispenser 850. The frequency and the amplitude of the vibration may be selected such that it promotes fluid transport with minimal generation of sound.

Optionally, fluid dispenser 850 can also include an electrode device 892. Electrode device 892 can be configured to apply an electric voltage to a therapeutic substance within ear canal EC to enable flow of the therapeutic substance through a tympanostomy tube. In some embodiments, electrode device 892 can be a separate device from fluid dispenser 850. Further details of an electrode device 892 are described below with reference to FIGS. 12A, 12B, 13A, and 13B.

Fluid dispenser 850 optionally can also include a positioning element 886. Positioning element 886 can be designed to help position and orient tip 884 and/or other components of fluid dispenser 850 (e.g., vibrating element 890) relative to ear canal EC. For example, positioning element 886 can be a flange that is configured to fit around a back of the ear to guide tip 884 into position in ear canal EC. In some embodiments, positioning element 850 can be configured to limit the insertion of applicator 880 into ear canal EC, thereby limiting over-insertion of applicator 880. In some embodiments, position element 850 can be or form a part of vibrating element 890 (e.g., vibrating element 890 can include a component that is designed to contact a region of a subject's ear and orient applicator 880 with respect to ear canal EC).

Figure 10:
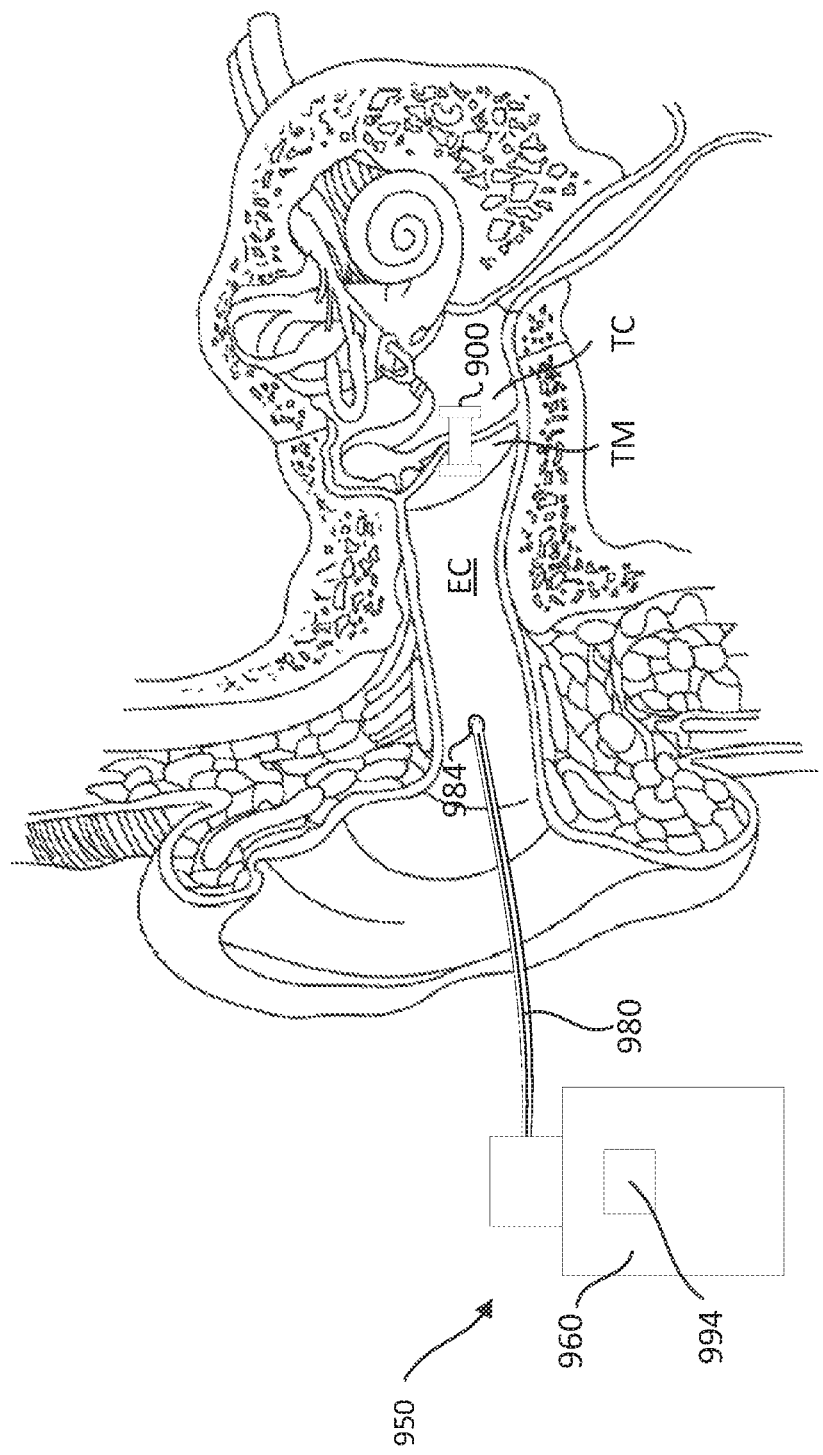
FIG. 10 is a schematic illustration of a fluid transport system disposed in an ear of a subject, according to some embodiments.

FIG. 10 illustrates an example fluid delivery system, including a fluid transport device 900, such as, for example, a tympanostomy tube, and a fluid dispenser 950. Fluid transport device 900 can be structurally and/or functionally similar to fluid transport device 100 or tympanostomy tubes 200, 300, 400, 500, and 600, described above. As depicted in FIG. 10, fluid transport device 900 can be deployed in a tympanic membrane TM.

Fluid dispenser 950 can include a body 960 that defines a reservoir (not depicted). A therapeutic substance can be contained within the reservoir, which can be in fluid communication with an applicator 980. Applicator 980 can include a tip 984 that is configured to deliver the therapeutic substance to ear canal EC. Tip 984 can include a plurality of spray holes that are capable of directing the therapeutic substance toward a region of ear canal EC that is proximate to fluid transport device 900 and tympanic membrane TM, such that the therapeutic substance can be transported via fluid transport device 900 into tympanic cavity TC. Similar to applicator 880 and tip 884, applicator 980 and tip 984 can deliver the therapeutic substance to the region of ear canal EC proximate to fluid transport device 900 and tympanic membrane TM without relying on gravity and/or user action, such as, for example, tragal pumping.

Applicator 980 can be flexible and capable of being adjusted by a user into a specific configuration for positioning at an opening of ear canal EC or within ear canal EC. Fluid dispenser 950 can also include an actuator 994 that can be actuated to dispense fluid from tip.

Figure 11A:
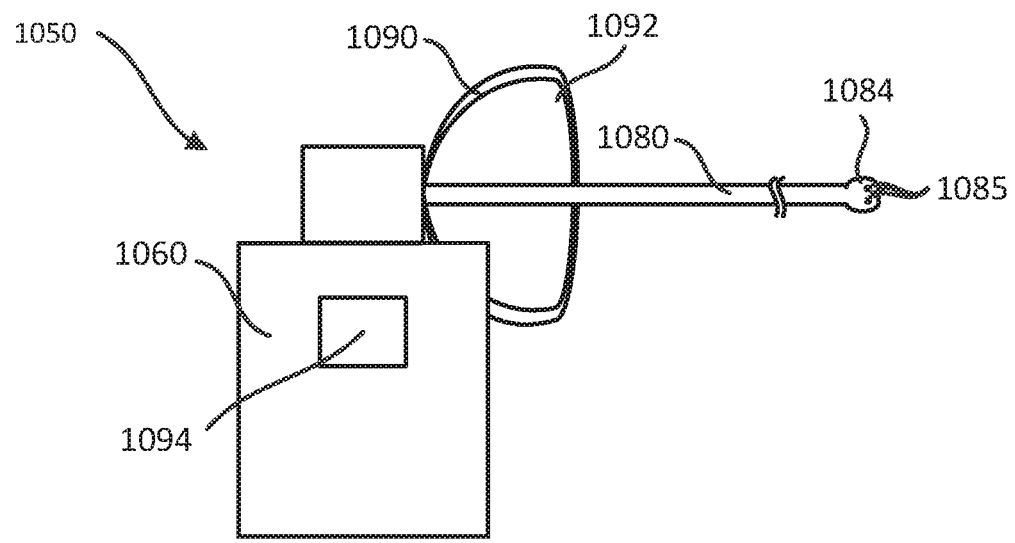
FIGS. 11A and 11B are schematic illustrations of a fluid dispenser or accessory device of a fluid transport system, according to some embodiments.
Figure 11B:
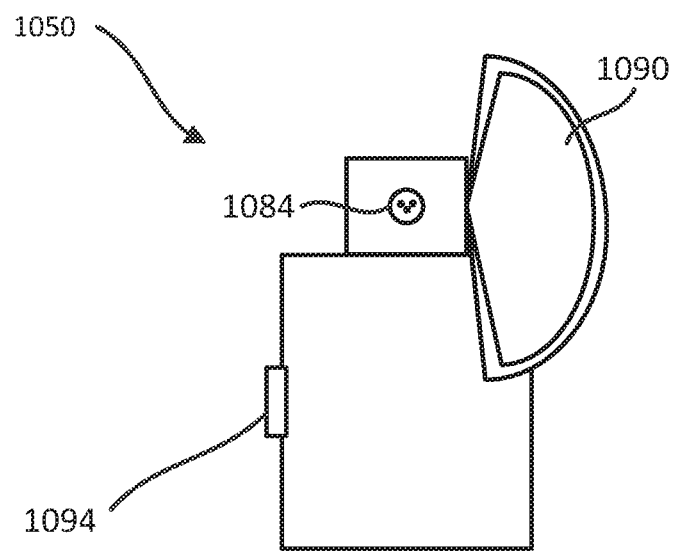

FIGS. 11A and 11B schematically depict an example of a fluid dispenser 1050, with a vibrating element 1080. Fluid dispenser 1050 can be used with a fluid transport device, such as, for example, fluid transport device 100 or tympanostomy tubes 200, 300, 400, 500, and 600, described above. Similar to fluid dispenser 950, fluid dispenser 1050 can include a body 1060, an applicator 1080, and a tip 1084. Tip 1084 can include a plurality of spay holes 1085, which can direct a therapeutic substance contained within a reservoir (not depicted) within body 1060 toward a target region (e.g., a region proximate to a tympanic membrane TM).

Fluid dispenser 1050 includes a vibrating element 1090 that is configured to engage with an area proximate to an ear of a subject. For example, vibrating element 1090 can include a surface 1092 that is shaped to fit or engage with an area of the ear or adjacent to the ear, such as, for example, the tragus and/or an area behind the ear over the mastoid bone. Vibrating element 1090 can impart a vibrating motion directly to the engaged area. Vibrating element 1090 can include a motor and a battery for powering the motor to provide the vibrating motion, or alternatively, be powered via a separate power source that is electrically connected to fluid dispenser 1050. Fluid dispenser 1050 can include an actuator 1094 that can be actuated to dispense fluid from tip 1084 and/or activate vibrating element 1090.

Figure 12A:
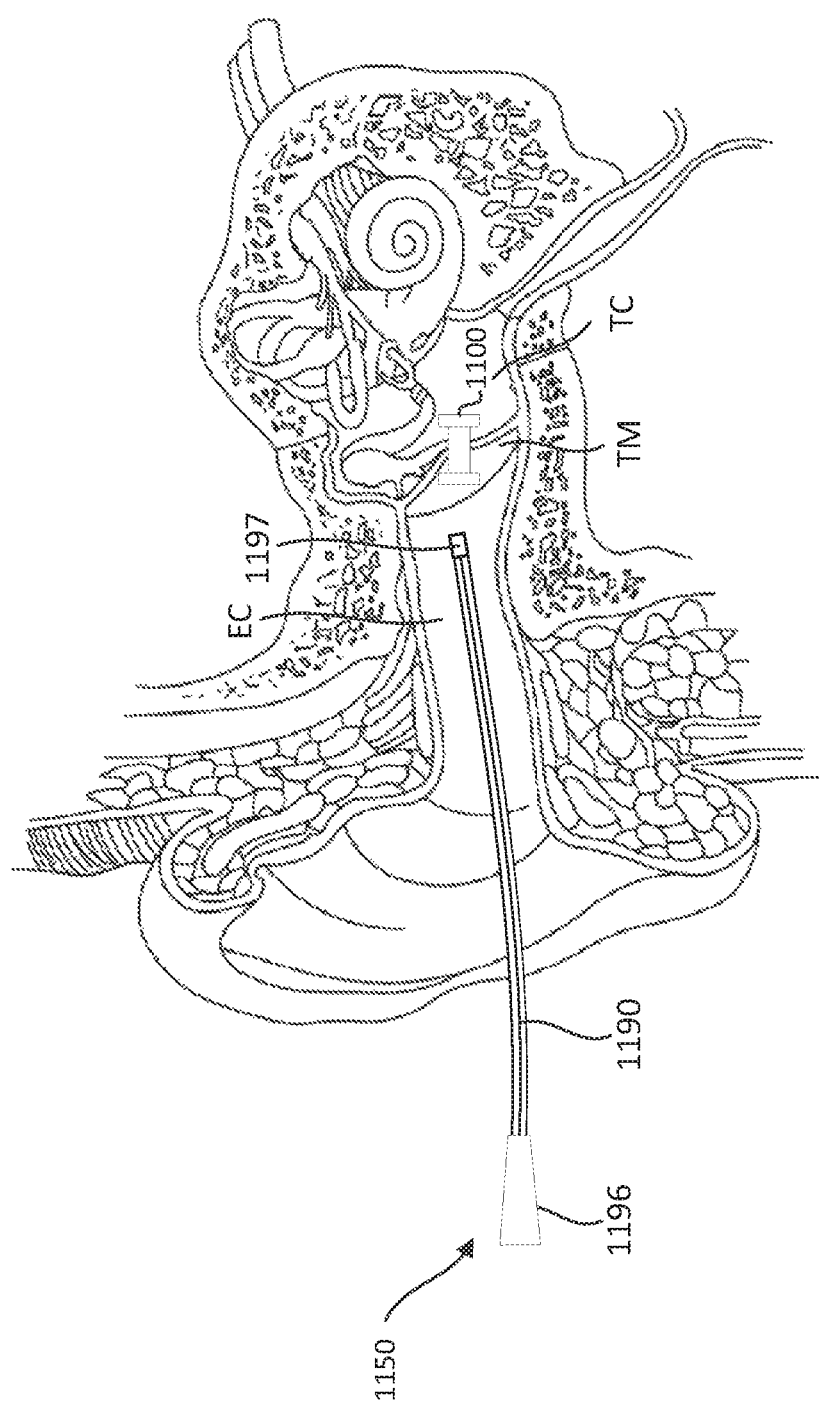
FIG. 12A is a schematic illustration of a fluid transport system disposed in an ear of a subject, according to some embodiments.
Figure 12B:
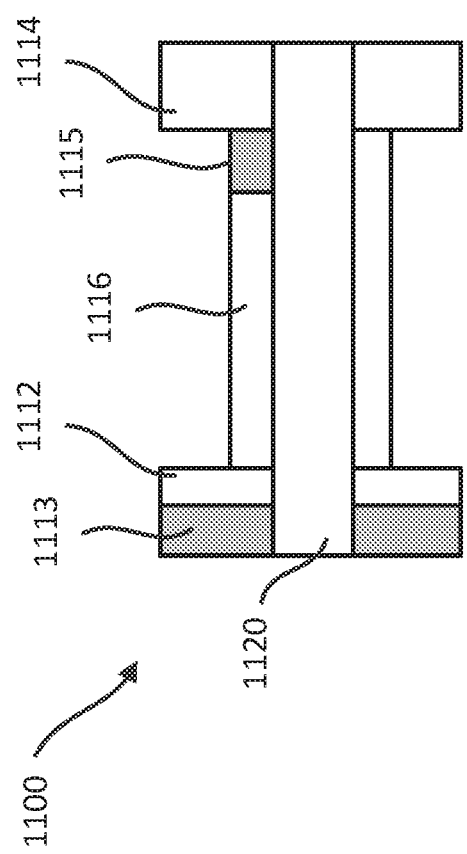
FIG. 12B is a schematic illustration of a fluid transport device of the fluid transport system illustrated in FIG. 12A, according to some embodiments.

FIGS. 12A and 12B schematically illustrate a fluid transport system including an accessory device such as an electrode device 1150. Electrode device 1150 can include an elongate shaft 1190, an electrode tip 1197, and a proximal connector 1196. Electrode device 1050 can also include a return electrode (not shown) that can be placed on the subject at a distance from electrode tip 1197. Electrode device 1150 can be dimensioned such that it can be inserted into ear canal EC of a subject, such as is shown in FIG. 12A. In some embodiments, electrode device 1050 can be flexible. Electrode tip 1197 can be constructed from a conductive material, such as, for example, a conductive metal. For example, electrode tip can be constructed from pure silver (e.g., 99.9% silver) and/or include a pure silver coating (e.g., a pure silver coating over a stainless steel electrode), which can provide reduced levels of electrolysis and changes in pH value when compared to other conductive materials such as, for example, stainless steel or gold. Electrode tip 1197 can have any general shape (e.g., cylindrical, rectangular, etc.).

Electrode tip 1197 may be attached to the elongate shaft 1190, e.g. by soldering or welding or by using a conductive adhesive. Elongate shaft 1190 can be constructed from a conductive material. In some embodiments, elongate shaft 1190 can be constructed from the same material as electrode tip 1197. Elongate shaft 1190 can be disposed within an outer sheath or sleeve. Outer sheath can be formed of a non-conductive, insulating material. In some embodiments, portions of electrode device 1150 (e.g., elongate shaft 1190) can be flexible or malleable such that a user can pre-shape electrode device 1050 before inserting it into ear canal EC. Elongate shaft 1090 can be attached to proximal connector 1096, which can be electrically connected to a source for providing energy to electrode device 1050. In other embodiments, electrode device 1050 can be wirelessly energized, e.g. using a magnetic field that can induce an electric current in one or more coils disposed on electrode device 1050.

Electrode device 1050 can be used to move the therapeutic substance across tympanic membrane TM into tympanic cavity TC via electrowetting. A tympanostomy tube 1100 deployed in tympanic membrane TM can have hydrophobic surfaces that limit and/or slow transport of a fluid, e.g., due to a large contact angle at which droplets of the fluid would contact the hydrophobic surfaces. Electrode tip 1197 can be used to apply a voltage to a conductive fluid containing the therapeutic substance to modify the contact angle that the fluid droplets have with surfaces of the tympanostomy tube 1100. Electrode tip 1197 can directly engage with one or more droplets of the conductive fluid and/or be used to apply an electric field via the conductive fluid and a conductive element disposed on tympanostomy tube 1100. FIG. 12B provides a detailed view of tympanostomy tube 1100. Similar to other tympanostomy tubes described herein, tympanostomy tube 1100 includes a lateral flange 1112, a tubular portion 1116 defining a lumen 1120, and a medial flange 1114. Tympanostomy tube 1100 includes a first conductive element 1113 disposed on lateral flange 1112, and a second conductive element 1115 disposed at a point along a length of tubular portion 1116.

When tympanostomy tube 1100 is deployed in tympanic membrane TM, a first electrical contact can be formed via the first conductive element 1113, the conductive fluid adjacent to tympanostomy tube 1100 within ear canal EC, and electrode device 1050. A second electrical contact can be formed via second conductive element 1115, which can engage with tissue within the ear to form the second electrical contact. Via the two electrical contacts, an electric field can be applied that can modify the contact angle that the fluid droplets have with surfaces of tympanostomy tube 1100. The strength of the magnetic field can be modified to control the flow characteristics of the conductive fluid containing the therapeutic substance through tympanostomy tube 1100.

Figure 13A:
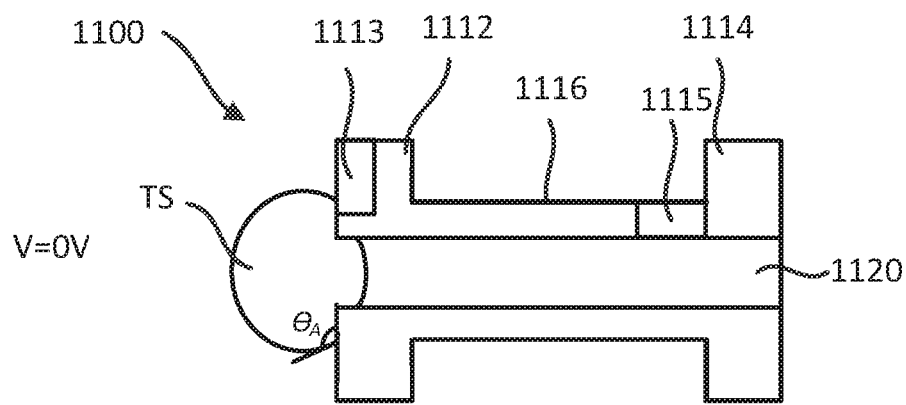
FIGS. 13A and 13B are schematic illustrations of a fluid transport device, according to some embodiments.
Figure 13B:
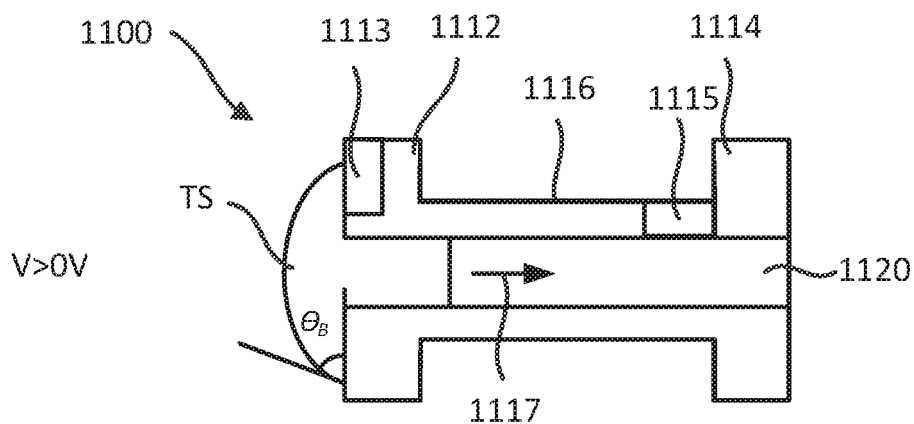

FIGS. 13A and 13B schematically illustrate the changes in a contact angle of a fluid droplet after application of an electric field. FIG. 13A depicts the contact angle when no electric field is applied, and FIG. 13B depicts the contact angle when an electric field is applied. As shown, an angle of contact $\Theta_A$ (when no electric field is applied) is greater than an angle of contact $\Theta_B$ (when an electric field is applied). The application of the electric field can enable transport of a therapeutic substance TS through lumen 1120 of the tympanostomy tube 1100 in a direction 1117.

Figure 14:
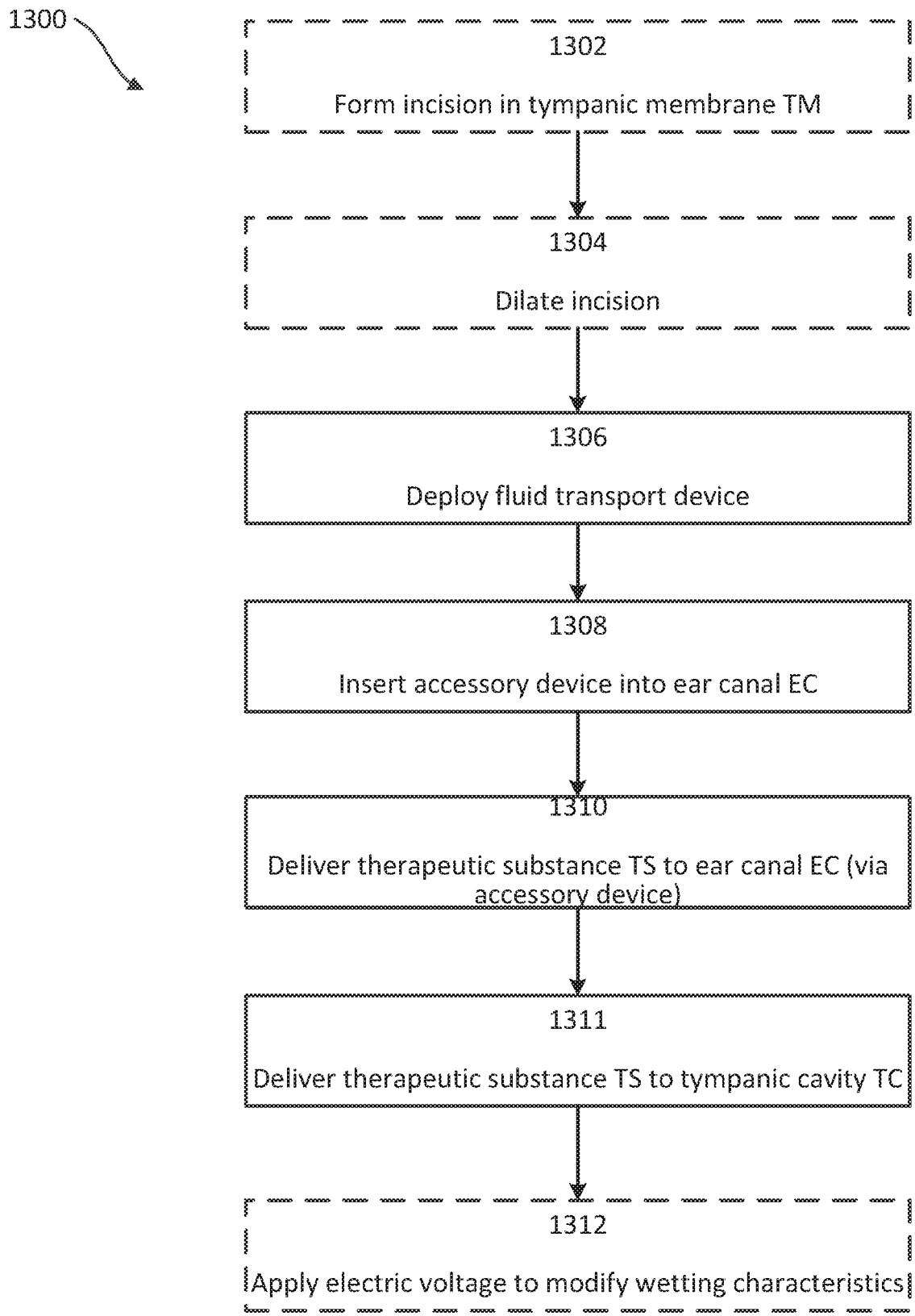
FIG. 14 is a flow diagram illustrating a method for transporting and delivering a therapeutic substance to a middle ear or tympanic cavity of a subject in accordance with some embodiments.

FIG. 14 is a flow diagram illustrating a method 1300 of transporting and delivering a fluid, such as a therapeutic substance to a tympanic cavity TC or the middle ear. To reach tympanic cavity TC, an incision IN through tympanic membrane TM is required. Incision IN may already have been created in a separate procedure on the subject, e.g. by a myringotomy or tympanocentesis to enable drainage of medial effusion, or by a tympanostomy in connection with delivery of a tympanostomy tube. Alternatively, formation of incision IN may be performed as an initial step 1302. Incision IN may be formed using any suitable technique and device.

Incision IN may also be dilated, either as part of a separate procedure, e.g., in connection with delivery of a tympanostomy tube, or as step 1304 of method 1300. The dilation can facilitate insertion of a fluid transport device, such as, for example, fluid transport device 100 or tympanostomy tubes 200, 300, 400, 500, and 600, as described above. Incision IN may be dilated using any suitable technique and device.

In step 1306, a fluid transport device, such as, for example, fluid transport device 100 or tympanostomy tubes 200, 300, 400, 500, 600, and 1100, as described above, is deployed. Deployment of fluid transport device can involve disposing fluid transport device into incision IN with a first portion of fluid transport device (e.g., a lateral flange or proximal end of fluid transport device) disposed on one side of tympanic membrane TM and a second portion of fluid transport device (e.g., a medial flange or a distal end of fluid transport device) disposed on the other side of tympanic membrane TM.

An accessory device, such as accessory device 850, a fluid dispenser 950 or 1050, or electrode device 1150, can be inserted into ear canal EC, at step 1308. Therapeutic substance TS then can be delivered to tympanic cavity TC, at step 1310, either via accessory device or separately, e.g., via a conventional ear drop dispenser. Therapeutic substance TS can be delivered via fluid transport device (e.g., fluid transport device 100 or tympanostomy tubes 200, 300, 400, 500, 600, and 1100) to tympanic cavity TC, at step 1311, via methods described above. Optionally, at step 1312, an electric voltage can be applied, e.g., via an electrode device (e.g., electrode device 892 that is part of an accessory device and/or a separate electrode device 1150) to modify wetting characteristics of a contact of a fluid with a surface of a tympanostomy tube to transport the therapeutic substance through a lumen of the tympanostomy tube.

Although FIG. 14 illustrates method 1300 as occurring in a certain order, the ordering of method 1300 can be modified. Additionally, certain of the steps can be performed concurrently in a parallel process when possible, as well as performed sequentially. For example, in some embodiments, step 1310 (delivering therapeutic substance to tympanic cavity TC) can be performed simultaneously with step 1312 (applying an electric voltage).

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The invention claimed is:

1. An apparatus, comprising:
   a tubular element configured to be deployed in a tympanic membrane, the tubular element including: a body having an outer surface and an inner surface, the inner surface defining a lumen, a first flange disposed on a proximal end of the body, and a second flange disposed on a distal end of the body; and
   a fluid transport element embedded in the body radially outwardly from the inner surface and configured to transport a therapeutic substance from the proximal end to the distal end of the body.

2. The apparatus of claim 1, wherein the fluid transport element includes a wicking material.

3. The apparatus of claim 1, wherein the fluid transport element extends from the first flange to the second flange.

4. The apparatus of claim 1, wherein a portion of the fluid transport element extends beyond the proximal end of the body such that the portion is disposed in an ear canal adjacent to the tympanic membrane when the tubular element is deployed in the tympanic membrane.

5. The apparatus of claim 1, wherein the fluid transport element covers an area of the first flange and an area of the second flange, the area of the first flange being greater than the area of the second flange.

6. The apparatus of claim 1, wherein the fluid transport element covers a substantial area of the first flange and less than an entirety of the second flange.

7. The apparatus of claim 1, wherein the fluid transport element includes a plurality of microfluidic channels configured to channel the therapeutic substance from the proximal end through the microfluidic channels to the distal end of the body.

8. The apparatus of claim 7, wherein each microfluidic channel from the plurality of microfluidic channels has a first geometry at the proximal end of the body and a second geometry at the distal end of the body, the first geometry different from the second geometry to promote different fluid flow characteristics from one another.

9. The apparatus of claim 1, wherein the fluid transport element is embedded in the body in radially inwardly spaced relation from the outer surface.

10. The apparatus of claim 1, wherein the fluid transport element includes a microfluidic channel having a first region provided as a single microfluidic channel and a second region provided as plurality of microfluidic channels, the first region transitioning to the second region.

11. The apparatus of claim 7, wherein each microfluidic channel extends from the proximal end of the body to the distal end of the body, with each microfluidic channel having a geometry adjacent the distal end of the body to form droplets of the therapeutic substance that can be delivered into a middle ear adjacent to the tympanic membrane.

12. An apparatus, comprising:
a tubular element configured to be deployed in a tympanic membrane, the tubular element including: a body defining a lumen, a first flange disposed on a proximal end of the body, and a second flange disposed on a distal end of the body; and
a fluid transport element embedded in the body and configured to transport a therapeutic substance from the proximal end to the distal end of the body, wherein the fluid transport element includes a plurality of microfluidic channels, wherein each microfluidic channel from the plurality of microfluidic channels has a first geometry at the proximal end of the body, a second geometry extending along a length of the body from the proximal end to the distal end, and a third geometry at the distal end of the body, the first geometry shaped to collect the therapeutic substance, the second geometry shaped to transport the therapeutic substance from the proximal end to the distal end, the third geometry shaped to form droplets of the therapeutic substance that can be delivered into a middle ear adjacent to the tympanic membrane.

13. A system, comprising:
a tympanostomy tube configured to be deployed in a tympanic membrane, the tympanostomy tube having a body with an inner surface defining a lumen, a fluid transport element embedded in the body and configured to transport a therapeutic substance from a proximal side of the tympanostomy tube to a distal side of the tympanostomy tube; and
a fluid dispenser including: a reservoir configured to contain the therapeutic substance; and a tubular element defining a lumen in fluid communication with an outlet, the lumen and the outlet configured to deliver the therapeutic substance from the reservoir to a region of an ear canal proximal to the tympanic membrane, such that the therapeutic substance can be delivered through the fluid transport element to deliver droplets of the therapeutic substance to a middle ear distal to the tympanic membrane.

14. The system of claim 13, further comprising a vibrating element configured to vibrate the ear canal to transport the therapeutic substance toward the region of the ear canal proximal to the tympanic membrane.

15. The system of claim 14, wherein the vibrating element is provided on the fluid dispenser.

16. The system of claim 13, further comprising an electrode device configured to apply an electric voltage to the therapeutic substance.

17. The system of claim 16, wherein the tympanostomy tube includes: a first conductive element disposed at a proximal side of the tympanostomy tube and configured to form a first electrical path; and a second conductive element disposed at a distal side of the tympanostomy tube and configured to form a second electrical path.

18. The system of claim 17, wherein the second conductive element contacts a tissue surface to form the second electrical path.

19. The system of claim 17, wherein the first conductive element is configured to be in electrical communication with the electrode device via the therapeutic substance, such that the first conductive element can form the first electrical path.

20. The system of claim 13, wherein the fluid transport element has a first geometry adjacent the proximal side of the tympanostomy tube and a second geometry adjacent the distal side of the tympanostomy tube, the first geometry different from the second geometry to promote different fluid flow characteristics of the therapeutic substance.

* * * * *